(12) United States Patent
O'Hare et al.

(10) Patent No.: US 9,857,163 B2
(45) Date of Patent: Jan. 2, 2018

(54) PARAMETRIC CONTROL OF OBJECT SCANNING

(71) Applicant: Hexagon Metrology, Inc., North Kingstown, RI (US)

(72) Inventors: Jonathan J. O'Hare, Warwick, RI (US); Stephen Darrouzet, West Warwick, RI (US)

(73) Assignee: Hexagon Metrology, Inc., North Kingstown, RI (US)

( * ) Notice: Subject to any disclaimer, the term of this patent is extended or adjusted under 35 U.S.C. 154(b) by 438 days.

(21) Appl. No.: 14/523,251

(22) Filed: Oct. 24, 2014

(65) Prior Publication Data

US 2015/0139381 A1    May 21, 2015

Related U.S. Application Data

(60) Provisional application No. 61/897,860, filed on Oct. 31, 2013.

(51) Int. Cl.
| | | |
|---|---|---|
| *A61B 6/00* | (2006.01) | |
| *G01B 11/00* | (2006.01) | |
| *G01N 23/04* | (2006.01) | |
| *G06K 9/52* | (2006.01) | |
| *G06T 5/00* | (2006.01) | |
| *H05G 1/10* | (2006.01) | |
| *G01B 15/04* | (2006.01) | |

(52) U.S. Cl.
CPC .......... *G01B 11/005* (2013.01); *G01B 15/045* (2013.01); *G01N 23/046* (2013.01); *G06K 9/52* (2013.01); *G06T 5/001* (2013.01); *H05G 1/10* (2013.01); *G06T 2207/10116* (2013.01)

(58) Field of Classification Search
CPC ......... A61B 6/032; A61B 6/542; A61B 6/488; A61B 6/463; A61B 6/466; A61B 6/469; A61B 6/481

See application file for complete search history.

(56) References Cited

U.S. PATENT DOCUMENTS

| | | | |
|---|---|---|---|
| 7,627,083 B2 | 12/2009 | Ross et al. | 378/58 |
| 8,155,429 B2 | 4/2012 | Scholz et al. | 382/149 |
| 8,229,061 B2 | 7/2012 | Hanke et al. | 378/20 |

(Continued)

FOREIGN PATENT DOCUMENTS

| | | | | |
|---|---|---|---|---|
| DE | 10 2010 000 473 A1 | 8/2010 | | G06B 15/00 |
| WO | WO 2012/059446 | 5/2012 | | G06T 7/00 |

OTHER PUBLICATIONS

Kruth et al., "Computed tomography for dimensional metrology", Elsevier, CIRP Annals—Manufacturing Technology (60), pp. 821-842, 2011

(Continued)

*Primary Examiner* — Dani Fox
(74) *Attorney, Agent, or Firm* — Sunstein Kann Murphy & Timbers LLP

(57) ABSTRACT

A method of measuring an object having associated geometric data and material data receives the geometric data and material data relating to the object, and controls an x-ray device to scan the object. The x-ray device operates in accordance with a plurality of operating parameters. The method then varies at least one of the operating parameters during the scan as a function of one or both the geometric data and the material data.

16 Claims, 6 Drawing Sheets

(56) References Cited

U.S. PATENT DOCUMENTS

| | | | |
|---|---|---|---|
| 9,025,855 B1 | 5/2015 | Christoph et al. | ... G01N 23/046 |
| 2004/0086076 A1* | 5/2004 | Nagaoka | ............... A61B 6/032 |
| | | | 378/4 |
| 2008/0107231 A1 | 5/2008 | Miyazaki et al. | .............. 378/12 |
| 2010/0254509 A1 | 10/2010 | Sugaya et al. | .................. 378/16 |
| 2013/0195239 A1 | 8/2013 | O'Hare et al. | .................... 378/4 |
| 2013/0235970 A1 | 9/2013 | Voland et al. | .................... 378/4 |
| 2014/0222373 A1 | 8/2014 | Sprenger | ...................... 702/155 |

OTHER PUBLICATIONS

International Preliminary Examining Authority, Written Opinion—International Application No. PCT/US2014/062165, dated Feb. 5, 2016, 6 pages.

Sunstein Kann Murphy & Timbers LLP, Amendment of Claims Under PCT Article 34 and Response to Written Opinion—International Application No. PCT/US2014/062165, as filed Aug. 17, 2015, 9 pages.

Sunstein Kann Murphy & Timbers LLP, Amendment of Claims Under PCT Article 34 and Response to Written Opinion—International Application No. PCT/US2014/062165, as filed Dec. 16, 2015, 10 pages.

International Preliminary Examining Authority, Written Opinion of the International Preliminary Examining Board—International Application No. PCT/US2014/062165, dated Oct. 16, 2015, 6 pages.

Liu et al., "*Optimal acquisition parameter selection for CT simulators in radiation oncology*", Journal of Applied Clinical Medical Physics, vol. 9, No. 4, pp. 151-160, Fall 2008.

Reiter et al., "*Study on Parameter Variation of an Industrial Computed Tomography Simulation Tool Concerning Dimensional Measurement Deviations*", Proceedings of the 10$^{th}$ European Conference on Non-Destructive Testing, Moskau, Russian Federation, 10 pages, 2010.

International Searching Authority, International Search Report—International Application No. PCT/US2014/062165, dated Feb. 12, 2015, together with the Written Opinion of the International Searching Authority, 11 pages.

* cited by examiner

PARAMETRIC CONTROL OF OBJECT SCANNING

PRIORITY

This patent application claims priority from provisional U.S. patent application No. 61/897,860, filed Oct. 31, 2013, entitled, "PARAMETRIC CONTROL OF OBJECT SCANNING," and naming Jonathan J. O'Hare and Stephen Darrouzet as inventors, the disclosure of which is incorporated herein, in its entirety, by reference.

FIELD OF THE INVENTION

The invention generally relates to measuring objects using CT systems and, more particularly, the invention relates to parameters required to scan an object using a CT system.

BACKGROUND OF THE INVENTION

Coordinate measuring machines (CMMs) are the gold standard for accurately measuring a wide variety of work pieces. For example, CMMs can measure critical dimensions of aircraft engine components, surgical tools, and gun barrels. Precise and accurate measurements help ensure that their underlying systems, such as an aircraft in the case of aircraft components, operate as specified.

Recently, those in the art have begun using computed tomography (CT) systems as CMMs for coordinate metrology. As known by those in the art, a CT system generates three-dimensional images of an object as a function of the attenuation of its x-rays by the object. Accordingly, a CT system scans the object, which typically is positioned on a moving platform, such as a rotary table. Before the scan, however, operators manually pre-program their CT systems with fixed operating parameters, such as the power required for generating the x-ray signals.

SUMMARY OF VARIOUS EMBODIMENTS

In accordance with one embodiment of the invention, a method of measuring an object having associated geometric data and material data receives the geometric data and material data relating to the object, and controls an x-ray device to scan the object. The x-ray device operates in accordance with a plurality of operating parameters. The method then varies at least one of the operating parameters during the scan as a function of one or both the geometric data and the material data.

The operating parameters may include at least one of voltage and current, and the x-ray device may have a scanner. In that case, the method may move the object relative to the scanner, and vary the current as a function of the position of the object relative to the scanner. This relationship alternatively could be described as the trajectory of the x-ray beam through the object. In addition to at least one of voltage and current, the operating parameters may include at least one of magnification, detector exposure time, image averaging, number of projections, and the region of interest in the field of view.

The method may vary the operating parameter(s) by receiving information about the operating voltage of the x-ray device based on the material data, and operating the x-ray device at the operating voltage. Moreover, among other things, the geometric data may be received via a 3D computer aided design (CAD) file having the geometric data.

In accordance with another embodiment, a method of measuring an object having associated geometric data and material data receives the geometric data and material data relating to the object; and controls an x-ray device to scan the object. The x-ray device operates in accordance with a plurality of operating parameters. The method also controls a parameter manager to determine the operating parameters as a function of at least one of the received geometric data and material data.

In accordance with other embodiments, a method of measuring an object positions the object to be scanned by an x-ray device having a scanner to scan the object, and receives geometric data relating to the object. The method also controls the scanner of the x-ray device to scan the object, and varies the power of the x-ray device during the scan as a function of the orientation of the object relative to the scanner. The method also varies the power of the x-ray device as a function of the geometric data relating to the object.

Among other things, the power may be a function of current, voltage, and/or exposure time of the object to the x-rays.

Illustrative embodiments of the invention are implemented as a computer program product having a computer usable medium with computer readable program code thereon. The computer readable code may be read and utilized by a computer system in accordance with conventional processes.

BRIEF DESCRIPTION OF THE DRAWINGS

Those skilled in the art should more fully appreciate advantages of various embodiments of the invention from the following "Description of Illustrative Embodiments," discussed with reference to the drawings summarized immediately below.

DESCRIPTION OF ILLUSTRATIVE EMBODIMENTS

In illustrative embodiments, an X-ray device varies its operating parameters while scanning an object. Specifically, the x-ray device varies its operating parameters as it is scanning the object based on pre-specified geometric and/or material information relating to the object. Accordingly, scans of high aspect ratio objects, among other types of objects, can produce improved output images. In addition, logic within the X-ray device calculates some or all of the operating parameters based on the geometric and/or material information—minimizing the need to manually determine such values. Details of illustrative embodiments are discussed below.

Figure 1:
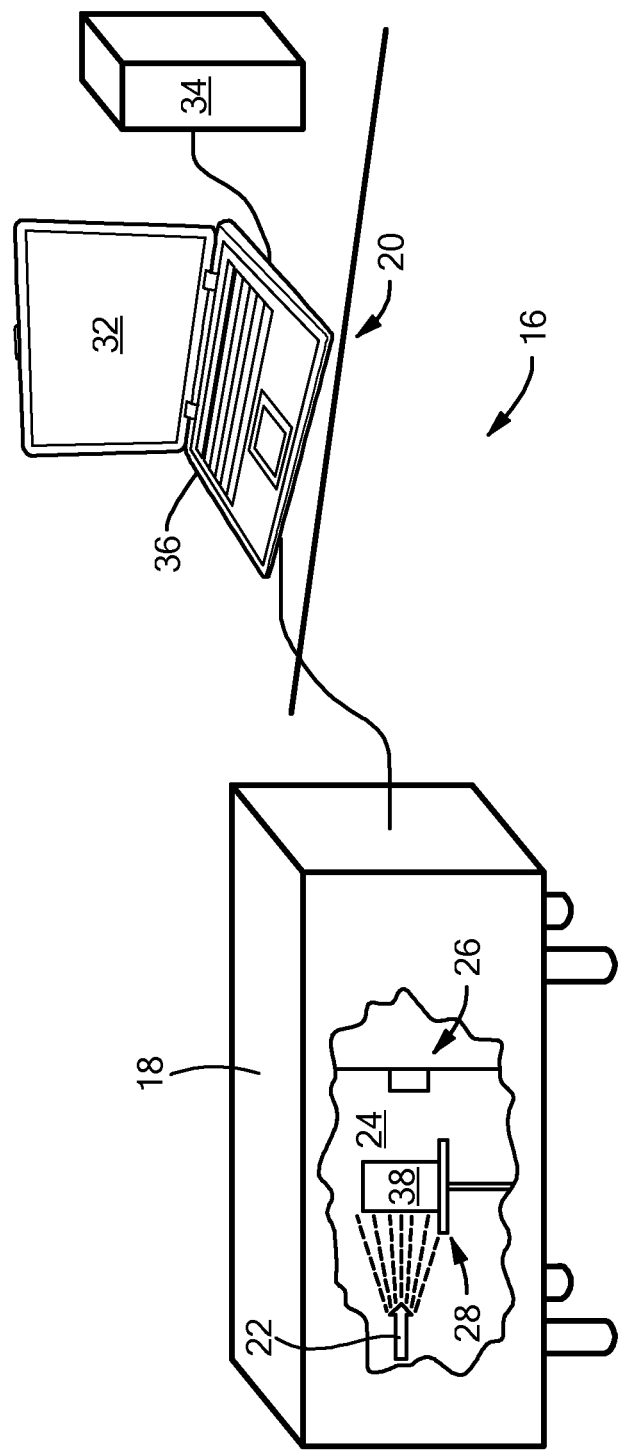
FIG. 1 schematically shows an imaging system that may be configured in accordance of illustrative embodiments of the invention.

FIG. 1 schematically shows an imaging and measurement system 16 that can generate an image of an object 10 in accordance with illustrative embodiments of the invention. As shown, the system 16 includes a computed tomography machine ("CT machine 18") coordinated and controlled by an accompanying computer system 20. The CT machine 18 is shown in a cut-away view to detail some of its interior components. Specifically, like others in the art, the CT machine 18 in this figure has an x-ray source 22 that transmits x-rays (typically) in a generally cone-shaped pattern (a/k/a "cone beam"), toward and through an object 10 within its interior region. This interior region, which contains the object 10 being imaged as it is receiving x-rays, is referred to herein as an "active region 24." As known by those skilled in the art, the object 10 attenuates the x-rays to some degree, changing the pattern of x-rays on the opposite side of the object 10. A detector 26 on the opposite side of the object 10 detects this pattern, producing a two-dimensional representation/image of the object 10.

To obtain a three-dimensional representation/image, however, the system 16 moves the position of the object 10 relative to the x-ray source 22 and detector 26. Some CT machines 18 rotate the x-ray source/scanner 22 and detector 26 (referred to as "source/detector pair 22/26") while leaving the object 10 stationary. Other CT machines 18 may rotate the object 10 and/or the source/detector pair 22/26. Of course, various embodiments may use these and other arrangements. In the latter case, the object 10 may be positioned on a rotating device, such as the platter of a rotary table 28 or fixture. Among other ways, the rotary table 28 may be configured to precisely rotate the object 10 a predefined amount each time it generates a two-dimensional image (discussed below). For example, the CT machine 18 may take 1000 to 2000 two-dimensional images of the object 10 on the table 28. As another example, the CT machine 18 may take 200 to 2000 two-dimensional images of the object 10 on the table 28. These two-dimensional images, which typically are taken from slightly different perspectives/orientations, often are referred to in the art as "projections."

Conventional software techniques convert this plurality of two-dimensional images/projections into a detailed, comprehensive three-dimensional representation of the object 10. For example, the computer system 20, which has a display device 32, a CPU/memory/logic within a chassis 34 (i.e., a computer), input device 36, and other conventional components, may execute these software routines to generate a three-dimensional representation of the object 10 (discussed below with regard to FIGS. 2 and 3). The computer system 20, however, also may execute other routines that improve scanning throughput.

Figure 2:
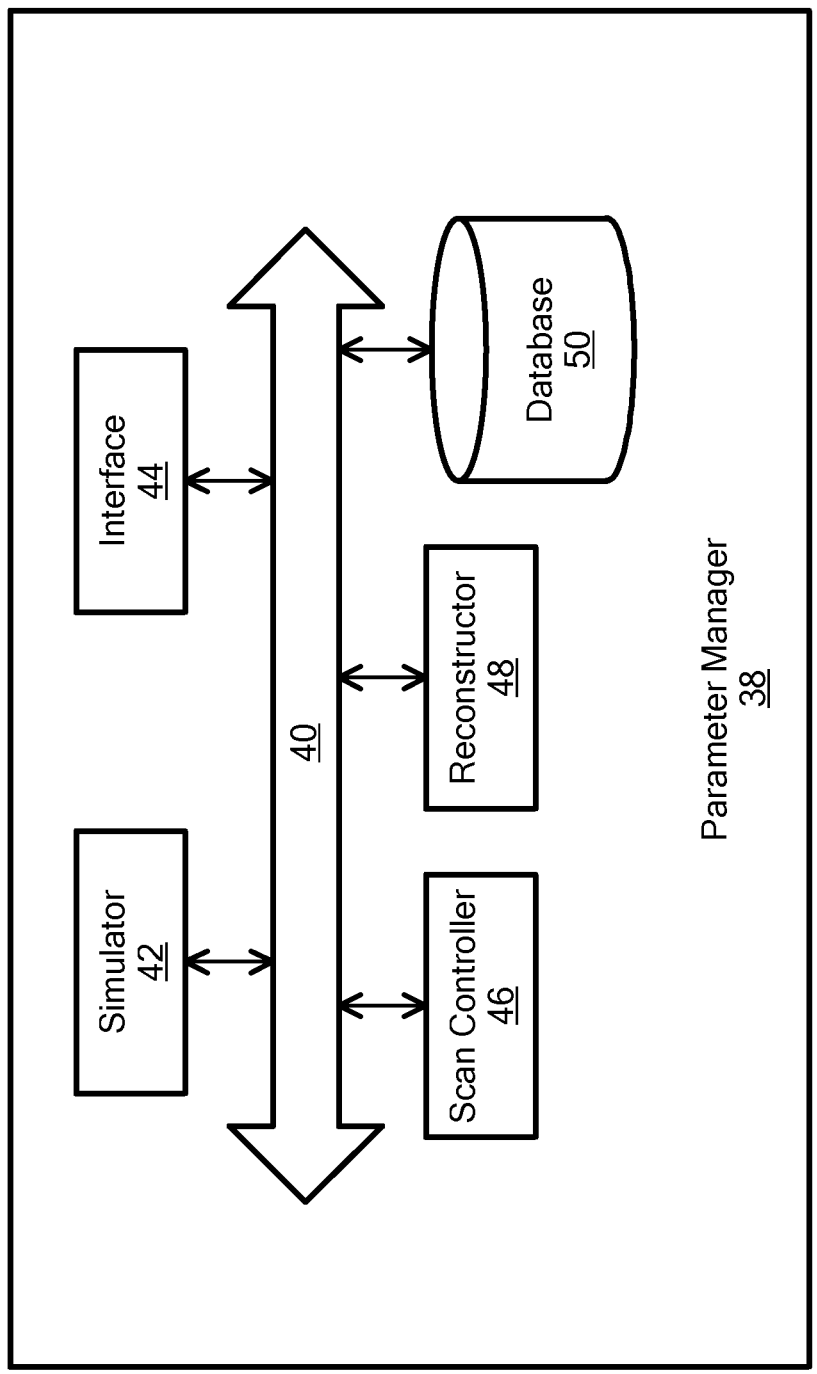
FIG. 2 schematically shows a parameter manager that may be configured in accordance with illustrative embodiments to control the scan parameters of the imaging system in FIG. 1.

FIG. 2 schematically shows a parameter manager 38 that controls the variability of the parameters. To that end, the parameter manager 38 has a general interconnect system 40 that electrically connects a plurality of functional parts that independently and/or with other functional parts control the parameters. Although the interconnect system 40 is shown in the drawing as a bus, those skilled in the art could use any of a wide variety of interconnection systems. Accordingly, discussion of a bus 40 is for simplicity purposes only.

Among the its primary portions, the parameter manager 38 has a simulator 42 for calculating the scanner trajectories required to capture the features of interest—either the entire object 10 or a part of the object. The simulator also receives input CAD model data and material data relating to the object 10, and then runs a number of simulated scans. The output of these scans may include the operating parameters used in actual scanning step(s).

The parameter manager 38 also has an interface 44 (i.e., an I/O port, which can include one port or a plurality of ports) to communicate with exterior devices, a scan controller 46 for controlling the scanner 22 in the CT-machine 18, and a reconstructor 48 for reconstructing an image of the object 10 from the plurality of two dimensional x-ray images. In addition, the parameter manager 38 also may have memory having a database 50 for storing trajectory and/or parameter data, such as a look-up table and/or equation specifying the variability of one or more parameters.

The noted functional parts 42-50 discussed above in the parameter manager 38 may be dispersed across multiple machines/devices (e.g., some may be in the computer system 20, others may be in the CT machine 18, while others may be other devices not shown in the figures. In fact, the functionality of a single one of the functional parts 42-50 may be distributed across multiple devices. Accordingly, discussion of a single parameter module 38 with all functional parts 42-50 in that single device is for simplicity purposes only. Those skilled in the art can appropriately provision the system to meet the needs and demands of the specific application.

As discussed below, the functional parts 42-50 may be implemented as software, hardware, firmware, or some combination thereof. For example, the database 50 may be implemented using conventional RAID (redundant array of independent disks) technology in a storage server, while the interface 44 may be implemented as a hardware module having a female portion shaped to receive a corresponding male connector that complies with a specific interconnect standard. As another example, the scan controller 46 may be implemented as a digital signal processor or an application specific integrated circuit programmed to perform the scan controlling function.

Figure 3:
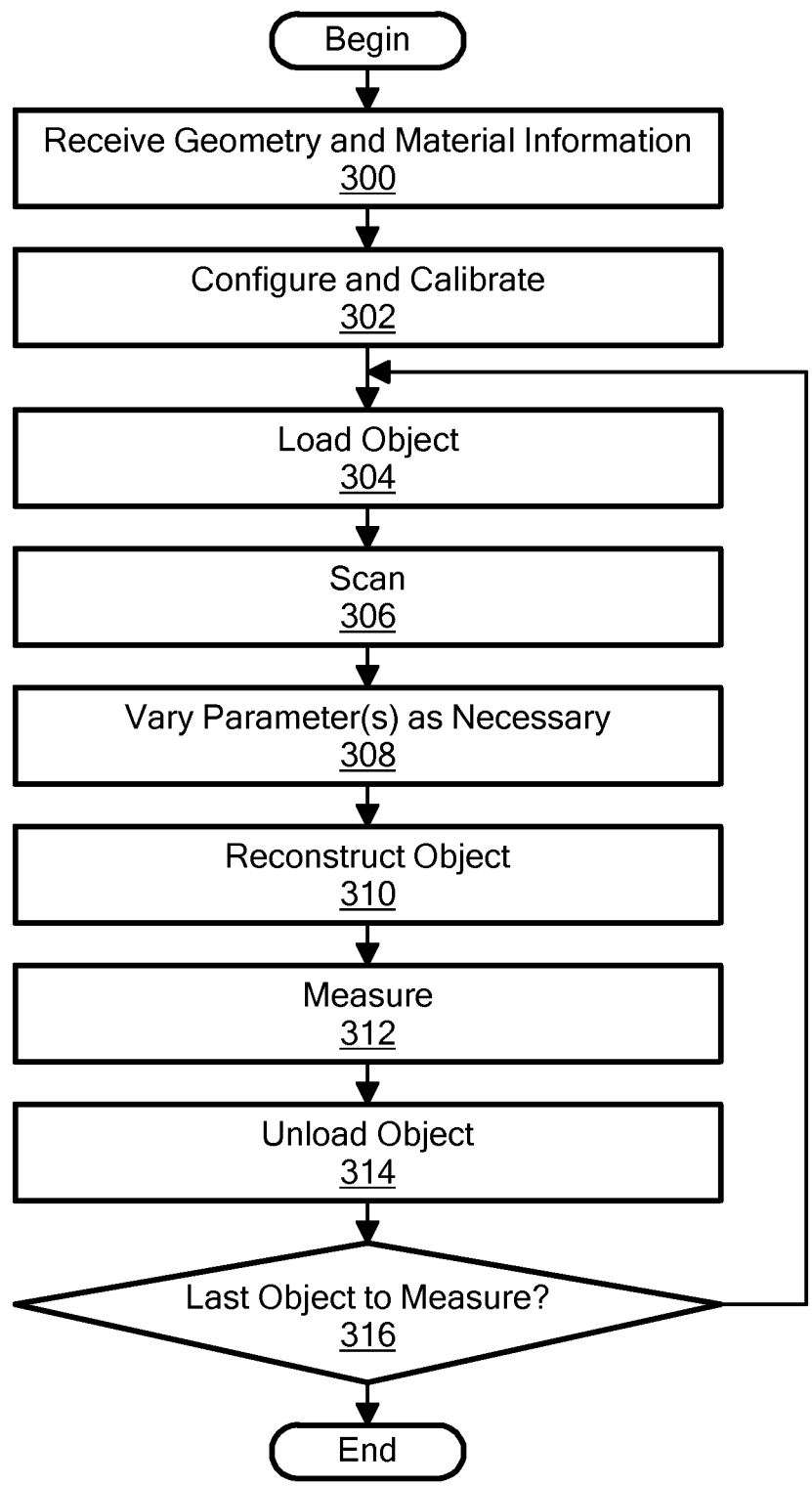
FIG. 3 shows a process of scanning an object in accordance with illustrative embodiments of the invention.

FIG. 3 shows a process of measuring the object 10 in accordance with illustrative embodiments of invention. In particular, this process varies at least one of the operating parameters during the scan as a function of one or both the geometric data and the material data of the object 10. In addition, although it can be used with a single object 10, this process preferably permits serial measurement of a plurality of like objects 10. For example, this process can be performed at the end of a production line to measure objects 10 (e.g., a specialized type of propeller) being manufactured.

It should be noted that this process is a simplified version of what could be a much longer process. Accordingly, the process may entail additional steps that are not discussed in FIG. 3. Moreover, some embodiments may perform various steps in a different order than that described. Those skilled in the art should be able to make appropriate changes to the order and number of steps in the process, and still meet the spirit of various embodiments.

The process begins step 300, which receives the geometry information and/or material information of the object 10 to be measured. Specifically, in a manner similar to many conventionally manufactured objects, prior to this process, the object 10 is manufactured according to a design specification with geometric (e.g., size, shape, etc.) and material requirements. For example, the material requirements may show that the object 10 is formed from a single material as a homogeneous part, or it may be formed from a plurality of materials (e.g., a two shot molded part, metal and plastic, silicon and metal, or other combination). These requirements may be stored at least in part within a computer aided design (CAD) file and/or some other type of file, either of which may be stored in some storage device associated with the system 16. Accordingly, since it is a process to measure the object 10, the process ultimately is performed to determine how close the actual geometry of the object 10 is to the idealized geometry specified by the CAD file (also referred to as the "CAD model," which can be retrieved dynamically or stored locally in some memory devices, such as in the memory storing the database 50). If the difference in certain aspects is outside of pre-specified tolerances, then the object 10 may be rejected. The parameter manager 38 may receive this information via its interface 44 for use by the simulator 42, scan controller 46, and its other functional parts 42-50 (e.g., the database 50).

The process then continues to step 302, which performs a number of configuration and calibration steps that permits the system 16 to repeatedly measure the same type of object 10 multiple times. To that end, the process registers the object 10 with a model of the object 10. Accordingly, using the registration information of the object 10 and the rotary table 28, the system 16 (e.g., perhaps using the reconstructor 48) registers the object 10 with the 3D CAD model. In other words, using the CAD model, the system 16 already has informational knowledge of the object 10 as it is positioned on the rotary table 28 (even if the object 10 is not yet loaded) and thus, uses the CAD model to identify nominal portions of the object 10 to scan.

This step continues by calculating efficient trajectories for the source/detector pair 22/26 to scan the object 10. In so doing, this step searches the nominal model for the features of interest, determines approximately where those features are located on the actual object 10, and then generates scanning trajectories to acquire visual indicia/data of the features of interest (or the entire object 10). In illustrative embodiments, step 302 loads the CAD model into the simulation program/simulator 42, which calculates trajectories that will capture the features of interest—either the entire object 10 or a part of the object 10. After calculating the trajectories, this step loads the desired trajectories into a controller (e.g., a part of the scan controller 46 or other part of the system) that controls the movement of the source/detector pair 22/26.

Part of step 302, including the details described immediately above, involves calculating various operating parameters for the system 16. In illustrative embodiments, the parameters are determined in the following order:

1. Voltage,
2. Magnification,
3. Current,
4. Detector exposure time,
5. Image averaging,
6. Number of projections, and
7. Region of interest in the field of view (also referred to as the "ROI").

Some embodiments do not determine the parameters in the order noted above. Moreover, some embodiments may control/configure using only some of these parameters, or use additional parameters. Accordingly, discussion of this specific order is for illustrative purposes only.

Each of these parameters is discussed briefly below.
Parameters

1. Voltage: the operating voltage, which is relevant to power, can be chosen based upon the material of the object 10. For example, in one system 16 known to the inventors, a plastic object 10 may require 70-110 kV, an aluminum object 10 may require 100-140 kV, and or a steel object 10 may require 140 kV or more. Heterogeneous objects 10 may require a more formulaic method for determine the voltage. Indeed, these ranges may vary on other systems and thus, are not intended to limit various embodiments. The National Institute of Standards and technology (i.e., "NIST") has a website that helps those skilled in the art plot the attenuation for a given material and for given x-ray energies.

In illustrative embodiments, the parameter manager 38 has a functional part (e.g., a controller, not shown) that can obtain this operating parameter by accessing a public database having these values. Some embodiments may directly access the NIST database, while others can store the information on a local database.

2. Magnification: Magnification of the image is an important limiting factor when determining a level of accuracy. As known by those in the art, among other things, the accuracy may be approximated by some ratio of the voxel size. For example, for 10 micron resolution, if the pixels on the detector 26 are 50 microns, then a 5× magnification may be required. If the detector 26 is 250 mm away from the source 22 and the object 10 is 50 mm away, then there is a 5× magnification. This is slightly complicated by systems 16 with wider ranges of magnifications because there may be multiple ways to achieve 5× magnification when both the object 10 and detector 26 can move. Whichever combination results in the detector 26 being closest to the source 22 generally is preferred (it often captures more x-rays that way, producing a stronger signal).

Accuracy and magnification data may be drawn from the CAD model. The CAD model preferably has the tolerances for the various features of the object 10, and the system 16 could use that information to determine an appropriate magnification.

3. Current: The thickness of the object 10 is relevant to the current required—and the power. For example, if the aspect ratio is large (thick in one dimension and thin in another, like a domino), then illustrative embodiments draw a lower current when imaging the thin part of the object 10, and a higher current when imaging the thick part of the object 10. Many sources 22 are characterized using a plot of total wattage vs. focal spot size of the source 22. The determination about an appropriate current depends upon a number of factors. For example, the system 16 may deliver a maximum amount of the current of the source 22 until (based on the characterization graph provided) the focal spot size becomes as generally large as the magnification sought (i.e., the magnification selected in an earlier step). If the voxel size is 10 microns, for example, a focal spot size of 3 microns may be too small—instead, it may be more advantageous to have a focal spot of about 9 microns to provide more flux.

In cases where the object 10 is more symmetrical, the system 16 does not necessarily require information about the object 10. As long as a correct voltage setting is used and there is an understood relationship of how the focal spot changes with wattage, then the x-ray current may be set to its maximum setting without affecting the focal spot. If the object 10 has a high aspect ratio, however, then the current preferably is changed on the fly/dynamically, as the object 10 is moving relative to the scanner/detector 22/26 (noted above).

4. Detector exposure time: The detector 26 may be at the fastest capture rate/minimum exposure time and the lowest number of averaged frames. If the contrast between the object 10 and the background is sub-optimal or poor, however, then illustrative embodiments slow down the detector exposure time to capture more x-rays per frame.

The detector exposure time and the current are related in that they both ensure sufficient contrast between the object 10 and the background. As long as the material and shape of the object 10 are known, and the system 16 is properly characterized, then logic should select the appropriate detector exposure time.

Moreover, as known by those skilled in the art, the detector exposure time can be considered to be a power value since a longer exposure results in an effective higher power. For example, exposure for 10 seconds at a power of A Watts should produce comparable results to exposure for 5 seconds at 2*A Watts. In both cases, the object 10 received essentially the same power.

5. Image averaging: Some embodiments do not require image averaging, such as when each frame is immediately saved as an image file for reconstruction. Other embodiments use averaging, which averages the pixel contrast values of a plurality of frames. For example, the system 16 may average twelve images. In that case, the system 16 may wait for the twelve images to be captured, combine the images, and then move the object 10 and/or detector 26 to the next position to gather another twelve frames. There are diminishing returns for averaging higher numbers of frames.

Image averaging is related to the noise level in the image, which is a function of the prior selected parameters. Illustrative embodiments use the other operating parameters and characteristics of the system 16 to determine this parameter. In alternative embodiments, image averaging may be determined independently for different projections or trajectories. Some orientations of the object may warrant more or less image averaging.

6. Number of projections: The number of images/projections collected for a given object 10 can vary—especially when used with non-traditional reconstruction algorithms. Specifically, the number of projections typically is based on the useful data around the object 10 about a single axis of rotation. Specifically, the system 16 typically is set to locate the largest width of the object 10 (the largest swept cylinder) and determine the number of pixels across the detector 26 that corresponds with that width (this is at the magnification to image the object 10). Those skilled in the art can select a reasonable number of projections, such as 1.2 times the number of pixels for the widest part of the object 10. A rough estimate should suffice as this parameter is less sensitive to error.

Illustrative embodiments primarily base the number of projections on the size and orientation of the object 10, and the magnification, which are known. The number of projections also may be reduced with knowledge of the shape and/or geometry of the object.

7. Region of Interest in the field of view: In simplified terms, the field of view is essentially whatever the x-ray beam contacts. It is common not to fill up the entire detector 26 while scanning an object 10, especially under low magnification. The capability of reconstructing the voxels containing the object 10 only, and the close, adjacent area should increase the subsequent reconstruction speed and reduce the file size of the data. In a manner similar to the number of projections, this parameter may be selected based on the size and orientation of the object 10 and magnification, which are known. Some embodiments may not process (i.e., not reconstruct) regions with voids of a scanned object if, in their CAD model, those regions indicate no material/a void, such as a bore or cavity that is an intended feature of the object.

Some of these parameters may be calculated and/or determined in any of a number of manners. In illustrative embodiments, the simulator 42, which can be executing on the computer system 20 or on the parameter manager 38, receives the input CAD model and material data, and then runs a number of simulated scans. The output of these scans includes the operating parameters (variable or static) that are used in actual scanning step(s). Other embodiments can use other ways to calculate/determine the parameters. For example, some embodiments may empirically determine the parameters through prior testing. In that case, the results of the testing can be stored in a database (e.g., in a look-up-table) for retrieval during scanning. Other embodiments may use data from prior scans. In either case, the system may employ machine learning techniques to improve the quality of the parameters.

Among other things, the parameters may be in the form of a range of numbers, a single number, or a function. For example, as discussed below, the current parameter may vary (or remain static, whichever the case may be) as a function of the orientation/position of the object 10 relative to the source 22. Other embodiments, however, may simply use some other means for determining the parameter. For example, as noted above, logic within the system 16, such as the scan controller 46, may simply access a look-up-table in the database 50 to determine one or more parameters, such as the voltage or magnification. In either case, manual interaction by an operator is not necessary since the system 16 determines these parameters in an automated manner. Other embodiments may involve an operator.

The set-up portion of the measurement/verification process is complete at this point. Now, the process may serially inspect many like objects 10. Specifically, at this point, the process may begin analyzing many different objects 10 that nominally have the characteristics of the object 10 in the CAD model. Stated another way, the process may now measure many objects 10 intended to have the features of the CAD model. Accordingly, steps 300 and 302 are considered to be "set-up" steps, while the remaining steps 304-316 form an inspection loop for capturing actual data relating to a plurality of like objects 10 and measuring the object using that actual data.

Accordingly, if not already within the machine 18, then the process continues to step 304 in which an operator (or some automated process) loads the object 10 into the CT scanning machine 18. More specifically, the operator precisely positions the object 10 on the rotary table 28 in a prescribed manner, effectively registering the object 10 with the rotary table 28. This enables the system 16 to readily associate various portions of the object 10 with the rotary table 28. In illustrative embodiments, the rotary table 28 does not block relevant portions of the object 10 being measured.

The process continues to step 306, which scans all or desired portions of the object 10 to produce visual indicia/data representing the object 10. During the scan, the process executes step 308, which, using the scan controller 46, varies one or more operating parameter as required (e.g., current, voltage, and/or exposure time). For example, the process may change the current as the object 10 is rotated generally about its axis to a thinner orientation. As another example, the detector exposure time may change when the object 10 is rotated to a thicker orientation. As a third example, the magnification may change as a scan is changed to a region of a large object 10 that does not need a detailed scan. Of course, other parameters may be changed and thus, discussion of the three above are merely used to illustrate various embodiments and not intended to limit various embodiments.

Illustrative embodiments may change these parameters on the fly—i.e., as the scan is taking place. The actual values of the changing parameters, however, may be determined before the scan begins in the set-up stage (steps 300-302). Specifically, some embodiments may pre-determine the operating parameters before the scan based on the factors discussed above, which should all be known before the scan. In that case, the system 16 has logic and memory (i.e., the parameter manager 38) that stores these values for retrieval at appropriate points of the scan. Other embodiments, however, may determine the operating parameter values during the scan. For example, the parameter manager 38 may use its scan controller 46 or other controller to determine the parameters during the scan, and quickly vary those parameters accordingly.

After scanning the appropriate portion or portions of the object 10, the reconstructor 48 then reconstructs the object 10 using conventional reconstruction processes known in the CT art (step 310). The system 16 may display the reconstructed object 10 on the display device 32, store it in memory, or both.

The process continues to step 312, which measures the feature or features of interest of the reconstructed object 10. Logic (not shown) or the controller (also not shown) may use conventional techniques for measuring portions of the reconstructed object 10. For example, if the object were a domino, then the controller may measure one or all of the length, width, and height of the domino as required by the application. The portions requiring measurement can vary widely based on user desires and the specific type of industry in which the object 10 is to be used. After the process measures the object 10, the operator or some automated mechanism unloads the object 10 (step 314) and determines if the object that was unloaded is the last object to measure (step 316). If the object 10 is not the last object 10 to be measured, then the process loops back to step 304, which loads another object into the CT machine 18. Alternatively, if at step 316 the object 10 is the last object 10 to be measured, then the process concludes. Accordingly, this process enables all objects 10 to be measured in a consistent, reliable manner.

Figure 4A:
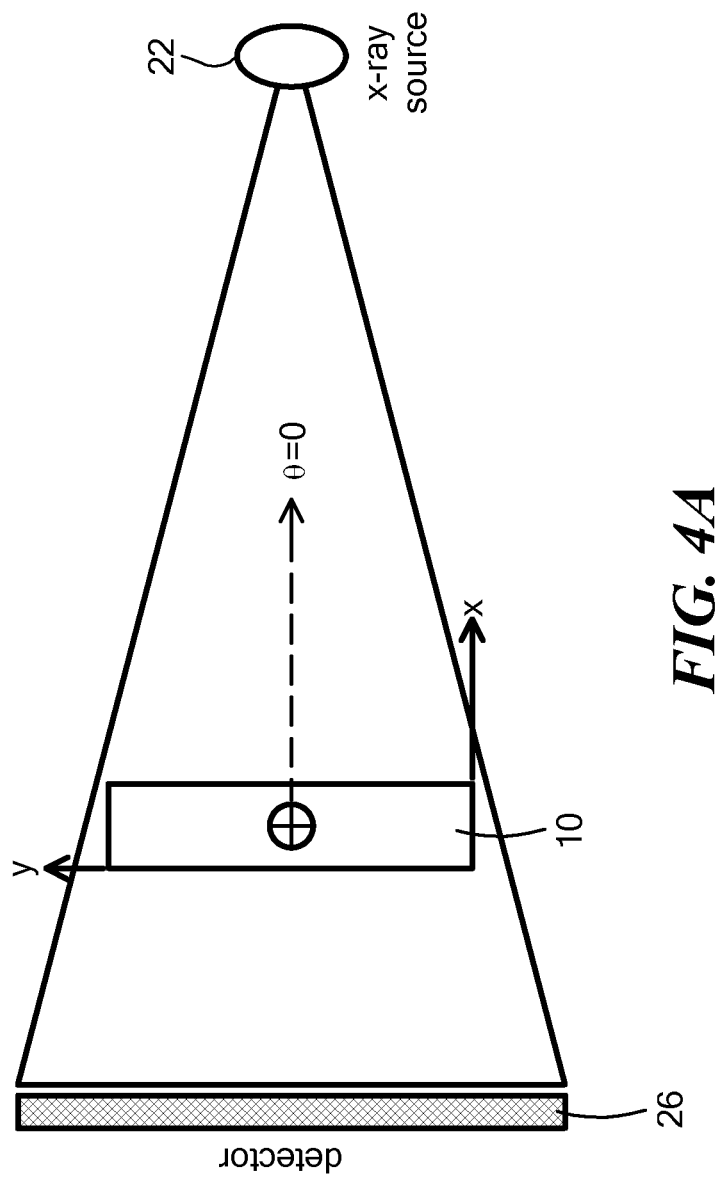
FIG. 4A schematically shows an exemplary object during a first part of a scan in accordance with illustrative embodiments.
Figure 4B:
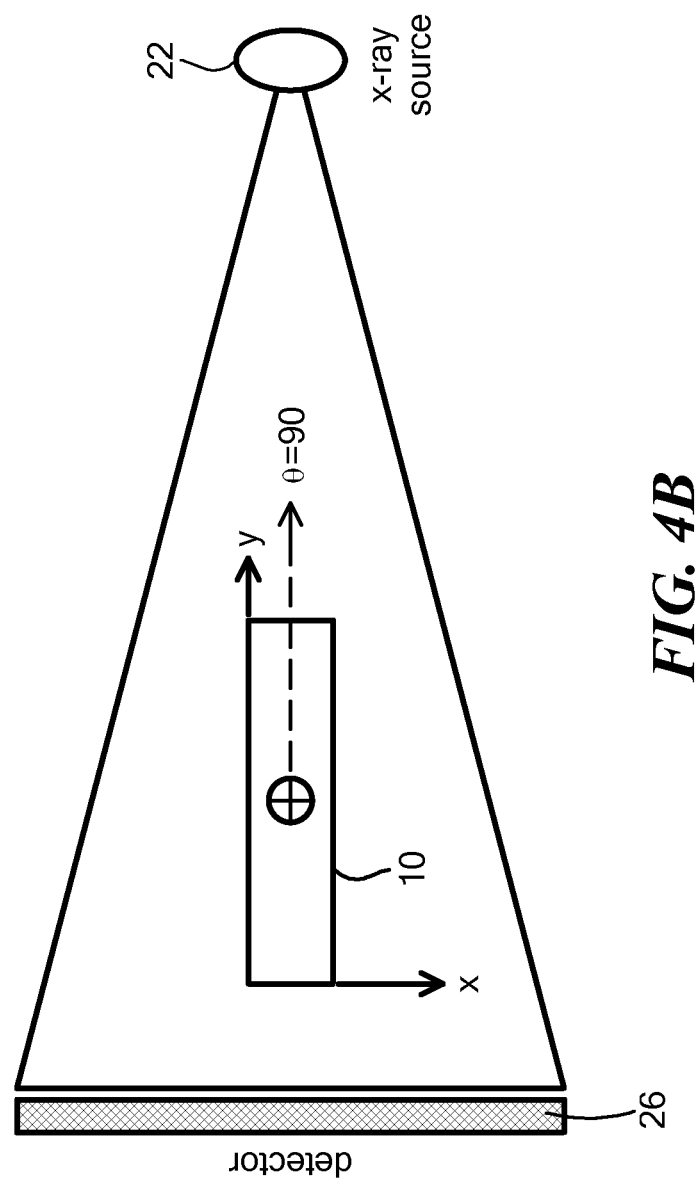
FIG. 4B schematically shows the object of FIG. 4A during a second part of the same scan.
Figure 4C:
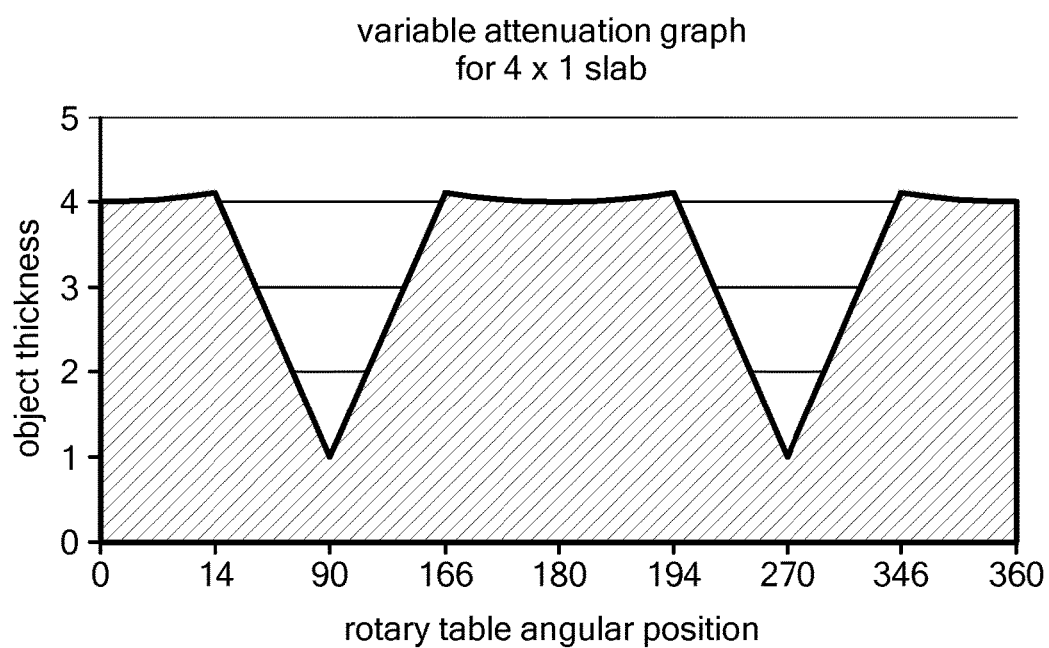
FIG. 4C graphically shows a variable attenuation graph of the object of FIG. 4A.

FIGS. 4A-4C schematically show at least part of this process using a simplified rectangular object having a length of 4 units (e.g., inches), a width of 1 unit, and a depth of 1 unit. This object 10 may be similar to the above noted domino example. For simplicity, this figure simply illustrates changes in power, voltage, current, and/or exposure time. In FIG. 4A, the object 10 is at its thinnest orientation, relative to the source 22. Accordingly, when the object 10 is in this orientation, the cone beam of the source 22 typically can most easily penetrate the object 10 in the X-direction (of the object 10). The x-ray power thus can be set, on the fly, to a lower setting in this case—perhaps a minimum power setting.

In FIG. 4B, however, the object 10 has rotated ninety degrees from its orientation in FIG. 4A to its thickest orientation relative to the source 22. Accordingly, when the object 10 is in this orientation, the source 22 typically can least easily penetrate the object 10 in the Y-direction (of the object). The x-ray power thus can be set, on the fly, to a higher setting in this case—perhaps a maximum setting. For example, the x-ray power may be increased up to a factor of its length/width (in this case, 4/1, or 4), or some other maximum.

FIG. 4C graphically shows the variable attenuation of this object 10 as it rotates a full 360 degrees on the rotary table 28. Illustrative embodiments may vary the power, current, and/or voltage, on the fly, in a manner corresponding with this graph. For example, as the rotary table 28 rotates along its 0-14 degree positions, the power may remain at a maximum. It should be noted that during that rotation interval, the power is not necessarily constant. When the rotary table 28 rotates the object 10 along its 14-90 degree positions, however, the power may drop at a steep slope to a minimum. The power may increase at a similarly steep slope as the rotary table 28 rotates the object 10 through the next range, 90-166 degrees, and continue controlling the power as shown.

It also should be noted that although a CAD model is described and discussed, those skilled in the art can use other types of models. Accordingly, discussion of a CAD model is for illustrative purposes only and not intended to limit all embodiments.

Various embodiments of the invention may be implemented at least in part in any conventional computer programming language. For example, some embodiments may be implemented in a procedural programming language (e.g., "C"), or in an object oriented programming language (e.g., "C++"). Other embodiments of the invention may be implemented as preprogrammed hardware elements (e.g., application specific integrated circuits, FPGAs, and digital signal processors), or other related components.

In an alternative embodiment, the disclosed apparatus and methods (e.g., see the various flow charts described above) may be implemented at least in part as a computer program product for use with a computer system. Such implementation may include a series of computer instructions fixed either on a tangible, non-transitory medium, such as a computer readable medium (e.g., a diskette, CD-ROM, ROM, or fixed disk). The series of computer instructions can embody all or part of the functionality previously described herein with respect to the system.

Those skilled in the art should appreciate that such computer instructions can be written in a number of programming languages for use with many computer architectures or operating systems. Furthermore, such instructions may be stored in any memory device, such as semiconductor, magnetic, optical or other memory devices, and may be transmitted using any communications technology, such as optical, infrared, microwave, or other transmission technologies.

Among other ways, such a computer program product may be distributed as a removable medium with accompanying printed or electronic documentation (e.g., shrink wrapped software), preloaded with a computer system (e.g., on system ROM or fixed disk), or distributed from a server or other remove device over the network (e.g., the Internet or World Wide Web). Of course, some embodiments of the invention may be implemented as a combination of both software (e.g., a computer program product) and hardware. Still other embodiments of the invention are implemented as entirely hardware, or entirely software.

Although the above discussion discloses various exemplary embodiments of the invention, it should be apparent that those skilled in the art can make various modifications that will achieve some of the advantages of the invention without departing from the true scope of the invention.

What is claimed is:

1. A method of measuring at least one object manufactured according to a design specification with associated nominal geometric data and material data, the method comprising:

loading a digital model of the at least one object having precise nominal geometric data of the manufactured object;

using the digital model to determine a plurality of features of interest of the manufactured object;

locating the features of interest of the manufactured object;

generating scanning trajectories for the features of interest of the manufactured object;

controlling an x-ray device to scan the manufactured object along the scanning trajectories for the features of interest of the manufactured object, the x-ray device operating in accordance with a plurality of operating parameters;

varying at least one of the operating parameters of the x-ray device during the scan of the features of interest of the manufactured object as a function of at least the precise nominal geometric data;

reconstructing no more than a portion of the manufactured object, the portion including the features of interest of the manufactured object; and measuring the features of interest in the reconstruction of the manufactured object.

2. The method as defined by claim 1 wherein the operating parameters include at least one of voltage and current.

3. The method as defined by claim 2 wherein the x-ray device includes a scanner, the method further comprising:
moving the manufactured object relative to the scanner; and
varying the current as a function of the position of the manufactured object relative to the scanner.

4. The method as defined by claim 1 wherein the operating parameters includes at least one of voltage, voxel size, magnification, current, detector exposure time, image averaging, number of projections, and region of interest in the field of view.

5. The method as defined by claim 1 wherein the x-ray device has an operating voltage, further wherein varying comprises:
receiving information about the operating voltage of the x-ray device based on the nominal geometric data and material data; and
operating the x-ray device at the operating voltage.

6. The method as defined by claim 1 wherein receiving comprises receiving a 3D CAD file having the nominal geometric data.

7. The method as defined by claim 1 wherein varying at least one of the operating parameters comprises varying the exposure time of x-rays of the x-ray device.

8. The method as defined by claim 1 further comprising positioning the manufactured object so that the x-ray device can scan the manufactured object.

9. The method as defined by claim 1 further comprising:
providing a plurality of additional objects that are nominally the same as the manufactured object, the plurality of additional objects each nominally having the same features of interest as the features of interest of the manufactured object;
controlling the x-ray device to scan the plurality of additional objects along the scanning trajectories;
varying at least one of the operating parameters during the scan as a function of one or both the nominal geometric data and the material data;
reconstructing the plurality of additional objects, each of the plurality of additional objects being no more than partly reconstructed and including the features of interest; and
measuring the features of interest in the reconstruction of the plurality of additional objects.

10. The method as defined by claim 9 wherein the additional objects are serially inspected using the providing, controlling, varying, reconstructing, and measuring acts.

11. A computer program product for use on a computer system for measuring at least one object manufactured according to a design specification, the at least one object having associated nominal geometric data and material data, the computer program product comprising a tangible, non-transient computer usable medium having computer readable program code thereon, the computer readable program code, when executed by a processor, causing the computer system to execute the acts comprising:
receiving at least one of the precise nominal geometric data and material data of a given object;
using the digital model to determine a plurality of features of interest of the given object;
locating the features of interest of the given object;
generating scanning trajectories for the features of interest of the given object;
controlling an x-ray device to scan the given object along the scanning trajectories for the features of interest of the given object, the x-ray device operating in accordance with a plurality of operating parameters;
varying at least one of the operating parameters during the scan of the features of interest of the given object as a function of one or both the precise nominal geometric data and the material data;
reconstructing no more than a portion of the given object, the portion including the features of interest of the given object; and
measuring the features of interest in the reconstruction of the given object.

12. The computer program product as defined by claim 11 wherein the operating parameters include at least one of voltage and current.

13. The computer program product as defined by claim 11, the computer program product being configured to inspect a plurality of additional objects that are nominally the same as the given object, the plurality of additional objects each nominally having the same features of interest as the features of interest of the given object, the computer program product having program code that further, when executed by the processor, causes the computer system to execute the acts comprising:
controlling the x-ray device to scan the plurality of additional objects along the scanning trajectories;
varying at least one of the operating parameters during the scan as a function of one or both the nominal geometric data and the material data;
reconstructing the plurality of additional objects, each of the plurality of additional objects being no more than partly reconstructed and including the features of interest; and
measuring the features of interest in the reconstruction of the additional objects.

14. The computer program product as defined by claim 13 wherein the additional objects are serially inspected.

15. The computer program product as defined by claim 11 further comprising comparing the measurements of the features of interest in the reconstruction with the precise nominal geometric data.

16. The method as defined by claim 1 further comprising comparing the measurements of the features of interest in the reconstruction with the precise nominal geometric data.

* * * * *